United States Patent [19]

Epstein

[11] Patent Number: 4,674,823
[45] Date of Patent: Jun. 23, 1987

[54] SOLAR RADIATION FILTER AND REFLECTOR DEVICE AND METHOD OF FILTERING AND REFLECTING SOLAR RADIATION

[76] Inventor: Michael Epstein, 1237 E. 72nd St., Brooklyn, N.Y. 11234

[21] Appl. No.: 622,996

[22] Filed: Jun. 21, 1984

[51] Int. Cl.⁴ .............................. G02B 5/28; G02B 5/26
[52] U.S. Cl. ..................................... 350/1.7; 350/615; 350/642
[58] Field of Search ................... 350/1.1, 1.5, 1.6, 1.7, 350/311, 642, 615

[56] References Cited

U.S. PATENT DOCUMENTS

| | | | |
|---|---|---|---|
| 3,382,183 | 5/1968 | Donoian et al. | 350/311 |
| 4,045,229 | 8/1977 | Weber, II et al. | 350/1.1 |
| 4,200,360 | 4/1980 | Mutzhas | 350/311 |
| 4,324,947 | 4/1982 | Dunbeck | 136/248 |
| 4,327,978 | 5/1982 | Wormser et al. | 350/320 |
| 4,332,239 | 6/1982 | Hotine | 126/425 |
| 4,332,240 | 6/1982 | Ward | 353/3 |
| 4,342,501 | 8/1982 | Solomon | 350/296 |
| 4,354,484 | 10/1982 | Malone et al. | 126/425 |
| 4,356,812 | 11/1982 | Hoven | 126/438 |
| 4,364,183 | 12/1982 | Rhodes | 33/268 |

FOREIGN PATENT DOCUMENTS

| | | | |
|---|---|---|---|
| 663136 | 4/1965 | Belgium | 350/615 |
| 1229268 | 9/1960 | France | 350/615 |
| 0017351 | 2/1978 | Japan | 350/311 |
| 812726 | 4/1959 | United Kingdom | 350/1.7 |
| 924686 | 5/1963 | United Kingdom | 350/615 |

*Primary Examiner*—Bruce Y. Arnold
*Attorney, Agent, or Firm*—Pennie & Edmonds

[57] ABSTRACT

Radiation filter and reflector device and method which filters certain bandwidths and reflects the transmitted bandwidths of incident radiation, in particular solar radiation. In a preferred embodiment of the device, it filters ultraviolet light below 320 nanometers and reflects all other wavelengths of sunlight. The preferred embodiment of the method comprises the steps of filtering ultraviolet light below 320 nanometers and reflecting all other wavelengths of sunlight. Both device and method provide the user with an effective sunscreen for preventing sunburn while affording tanning.

37 Claims, 3 Drawing Figures

SOLAR RADIATION FILTER AND REFLECTOR DEVICE AND METHOD OF FILTERING AND REFLECTING SOLAR RADIATION

BACKGROUND

This invention relates to a device and method for filtering certain bandwidths and reflecting the transmitted bandwidths of incident radiation, in particular solar radiation. In one embodiment shown here by way of example, the device and method filter ultraviolet sunlight and transmit and reflect all other wavelengths of sunlight and thereby provide individuals with an effective sunscreen for preventing sunburn while affording tanning.

Ultraviolet light has several beneficial effects. In addition to the cosmetic value of tanning, ultraviolet light can promote the healing of wounds and various skin diseases. Moreover, when ultraviolet light strikes the human body, it produces vitamin D, which is essential for the normal growth of bones. However, too much exposure of the body to ultraviolet light can be harmful. For example, prolonged exposure of the body to ultraviolet light can result in a reddening of the skin which is known as erythema or, more commonly, sunburn. In addition, excessive exposure of the body to ultraviolet light is a major cause of skin cancer. Moreover, excessive, long-term exposure of the body to ultraviolet light promotes severe deterioration of the epidermis. Frequently, weather-beaten, wrinkly, furrowed, splotchy, excrescence-marred faces characteristic of extreme old age develop in early middle age or sooner as a consequence of too much ultraviolet light.

Extensive studies have been made of the effects on the human skin of ultraviolet radiation in sunlight. With respect to erythema, Koller teaches that radiation between 280 and 320 nanometers produces substantially all of the erythemal (i.e., sunburn) effects and a substantial portion of the tanning effects. The maximum erythemal effect occurs at 296.7 nanometers. (L. Koller, *Ultraviolet Radiation*, Chap. 7, pp. 226–232, 2nd ed.) Radiation between 320 and 400 nanometers, the near ultraviolet, is pigmentogenic but not erythemogenic, and promotes tanning.

One technique for preventing harmful erythemal effects of ultraviolet light is to limit the exposure of the skin to the erythemogenic range of sunlight radiation to dosages less than those required to produce tanning. This technique, however, does not fit into the designs of a culture which enjoys outdoor activity and admires melanization of the skin through insolation.

Avoidance of exposure, however, is not necessary with the use of commercially available ultraviolet screening agents which mitigate the effects of exposure to erythemal radiation. These agents are typically in the form of a cream or lotion. When applied to the skin, these agents attenuate the dosage of erythemogenic radiation reaching the skin and thereby provide the user with some protection against the more harmful wavelengths of erythemal radiation.

The degree of protection provided by such agents is generally evaluated on the basis of exposure to summer noon-time sun for a four-hour period. To provide fast tanning with minimal protection, the agent should permit approximately 10–18 percent of the total erythemal flux of sunlight to reach the skin in the four-hour period. For regular protection and tanning, 6–12 percent of the total erythemal flux should reach the skin. For extra protection, only 1–6 percent of the total flux should reach the skin. Finally, for a total blocking effect, less than 1 percent should reach the skin.

Commercially available sunscreen agents provide these degrees of protection in various manners. For example, these agents typically comprise individual species or mixtures of chemicals such as salicylates, para-aminogenzoates, cinnamates, naphtholates, gallates, and benzophenomes in a primarily oily medium. By adjusting the concentration of the individual species or mixtures of chemicals, these agents can provide any degree of sunburn protection.

These agents, however, have several drawbacks. For example, a screening agent should demonstrate a relatively sharp absorption cutoff at 320 nanometers so that it transmits the maximum tanning radiation at wavelengths above the erythemal range. Unfortunately, the absorption spectrum of many commercially available agents extend into the tanning range and filter non-harmful tanning energies from the radiation. As a result, these agents have a very poor tanning efficiency.

Other drawbacks of these agents derive from their being in the form of lotions or creams which are applied directly to the skin. Although primarily oily, these agents are still soluble in water. Thus, perspiration of the user can dilute the agents or even completely wash them off, greatly reducing their effectiveness. In addition, the susceptibility of the chemicals in the lotion or cream to chemical and photochemical changes further decreases their ultraviolet absorbent effectiveness. Because it is difficult for the user to apply these agents to the body so that they form a continuous film of even thickness on the skin, they fail to promote uniform tanning. Moreover, the chemicals in these agents frequently exhibit unpleasant odors.

As lotions or creams, these agents are easily absorbed through the skin. As a result, they can cause pathological side effects such as irritation, allergic responses, melanosis, and trophic changes in the skin, in addition to interfering with normal growth and metabolic processes of the skin and mucous membranes and associated organs. In addition, these agents may stain or cause residual staining to skin and clothing, especially in the presence of sunlight, heat, laundry detergents, perspiration, etc.

SUMMARY OF THE INVENTION

In the present invention, I have devised a device for filtering certain bandwidths and reflecting the transmitted bandwidths of incident radiation, in particular solar radiation. In one embodiment, the device filters ultraviolet sunlight and transmits and reflects all other wavelengths of sunlight. When used by an individual as a tanning device, it provides the user with an effective sunscreen device for preventing sunburn while affording tanning.

In accordance with my invention, the device comprises a filtering layer and a contiguous reflecting layer. The filtering layer comprises material which has a predetermined absorptivity bandwidth to attenuate all wavelengths in that portion of the incident radiation. The reflecting layer is combined with the filtering layer to reflect those wavelengths of the incident radiation that are transmitted through the filtering surface.

In one preferred embodiment for use in suntanning applications, the device is used to filter harmful erythemal energies of sunlight while reflecting tanning energies to the skin of the user. In this embodiment, a layer of material is provided for filtering a certain bandwidth of ultraviolet light. This filtering layer comprises a layer of material having a relatively high ultraviolet light absorptivity. In particular, the material attenuates that portion of the incident solar radiation occurring at wavelengths shorter than 320 nanometers. The filtering layer is therefore configured as a low pass filter which advantageously filters off substantially all the erythemal energies while transmitting tanning energies.

In addition, a reflecting layer of material is provided for reflecting the bandwidths transmitted by the filtering layer. The reflecting layer comprises a base layer having a reflective surface layer. The base layer comprises any rigid material and provides support for the reflective surface layer. The reflective surface layer comprises a highly reflective material which is either evaporation deposited onto the base layer or, if independently rigid, then bonded to the base layer. In the preferred embodiment, the reflecting layer is bonded to the filtering layer with a transparent bonding agent so that the reflective surface layer lies contiguous to the filtering layer.

In a second preferred embodiment, the reflecting layer does not have a base layer. Instead, the layer of reflective material is evaporation deposited onto the filtering layer or, if independently rigid, bonded directly to the filtering layer with a transparent bonding agent.

To use the device, the user orients the outer surface of the filtering layer and hence the reflective surface of the reflecting layer at such an angle to the solar radiation that the radiation reflected by the device strikes the segment of the body to be tanned. When used in this manner, the device advantageously provides the body segment with optimum tanning energies from sunlight and optimum protection from the sun's erythemal energies.

Advantageously, any material capable of absorbing ultraviolet light can be used as the filtering surface. Typical filter materials include the following, either alone or in combination: glass, lithium fluoride crystalline, "pyrex" numbers 9700 and 9741, para-aminobenzoic (b 5 percent alcohol solution), ortho-aminobenzoates, anthranates, orthohydroxy benzoates, salicylates, 2-hydroxy-4 methoxybenzophenome (1 to 5 percent aqueous) solution, and 2-prime hydroxy-5 prime methyl phenyl benzotriazole (1 to 5 percent aqueous) solution. Because these materials are easily configured to have a sharp absorption cutoff frequency, they advantageously assure maximum transmission of desired tanning radiation at wavelengths above this cutoff frequency. In addition, by varying the thicknesses of these filter materials, the device can be advantageously "tuned" to provide any percentage attenuation of ultraviolet radiation that the user desires.

Because the device is not a lotion or cream, many of the drawbacks of conventional ultraviolet screening agents are avoided. For example, it cannot be diluted or washed off by perspiration of the user and therefore provides continuous and uniform filtering, regardless of the user's body condition. In addition, the device does not stain or cause residual staining to skin and clothing as conventional agents sometimes do. Moreover, unlike conventional agents, the device is odorless.

Because the device does not contact and become absorbed into the skin of the user, the device advantageously provides optimum tanning and sunburn protection without the pathological side effects sometimes caused by lotions or creams. Thus, the user can use the device without fear of irritation, allergic responses, melanosis, trophic changes in the skin, or interference with normal growth or metabolic processes of the skin and mucous membranes and associated organs. In addition, the device can comprise any material which absorbs ultraviolet radiation, unlike lotions or creams which are limited to materials that do not produce pathological side effects in the user. As a result, the long-term tanning efficiency and service life of the device can be optimized by the selection of filter materials that are resistant to the chemical and photochemical changes that are the primary cause of reduced long-term tanning efficiencies and service life in conventional tanning devices or agents.

With respect to both embodiments, the initially planar surface of the device is fabricated to comprise one or more panels. In a preferred embodiment, the device comprises three panels, two outer panels which are shaped in the form of a quadrilateral and a central panel which is shaped in the form of a trapezoid having parallel top and bottom edges. The panels are fabricated by creasing the initially planar device at two points along the width of the device such that the two creases extend the length of the device. By moving the outer panels about their respective creases, these outer panels can be angulated with respect to the central panel to advantageously conform to the shape of any body segment that a user of the device desires to tan.

The present invention also advantageously provides a method of filtering radiation comprising the step of filtering from an incident radiation spectrum emitting from a source an absorption spectrum having a bandwidth of wavelengths corresponding to the bandwidth of wavelengths desired to be filtered and the step of reflecting all other bandwidths of wavelengths. In a preferred method for preventing sunburn, the method comprises the additional step of filtering all wavelengths having a bandwidth of less than 320 nanometers.

BRIEF DESCRIPTION OF DRAWINGS

These and other objects, features, and advantages of the invention will be more readily apparent from the following description of the preferred embodiments of the invention in which.

DESCRIPTION OF PREFERRED EMBODIMENTS

Figure 1:
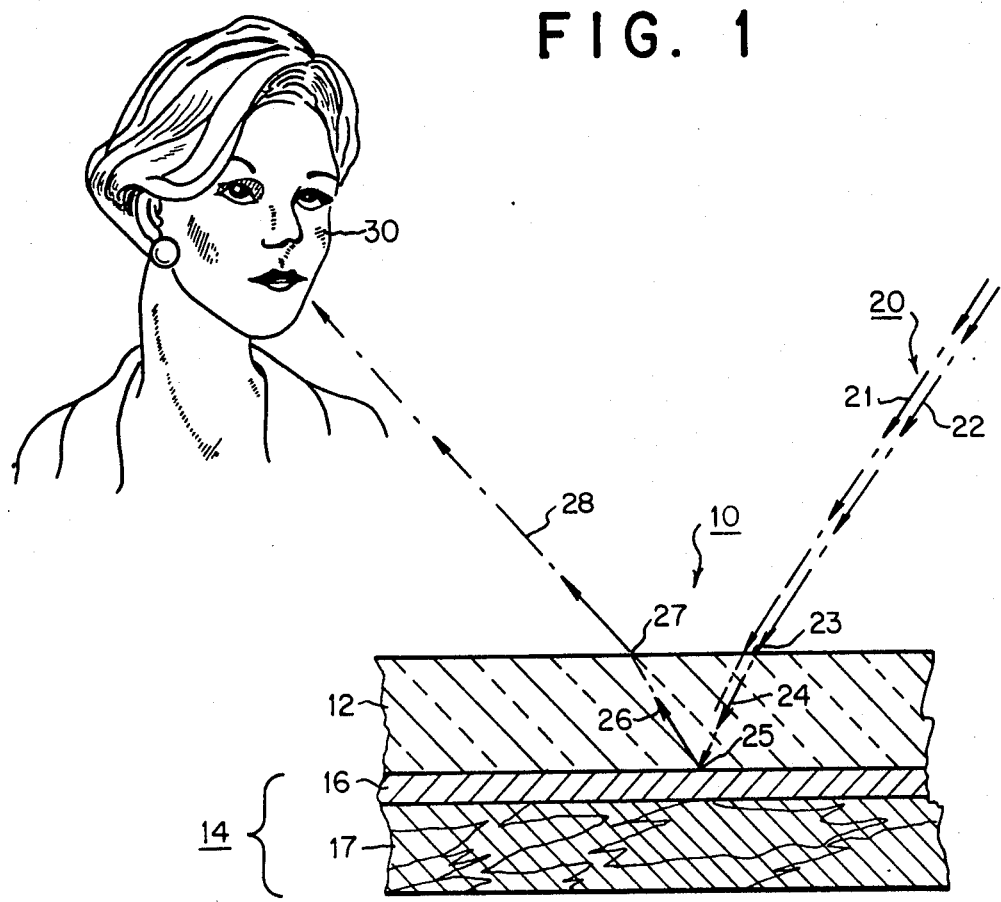
FIG. 1 is a cross-sectional view of a preferred embodiment of the present invention.

FIG. 1 shows a cross-sectional view of a preferred embodiment of a device 10 comprising filtering layer 12 and reflecting layer 14. As shown in FIG. 1, an incident beam of solar radiation 20 falls on filtering layer 12 at point 23. The beam contains two bands of wavelengths, band 21, which contains radiation having wavelengths below 320 nanometers, and band 22, which contains the remaining wavelengths in the solar radiation spectrum. As shown in FIG. 1, band 21 of incident beam 20 is terminated by the time it reaches point 25 of device 10. Band 22 travels through filtering layer 12, first as beam 24 to point 25, where it is reflected by reflecting layer 14, and then as beam 26 to point 27, where it leaves device 10 as beam 28 and shines on the face of a person 30.

Filtering layer 12 comprises a layer of glass or other material which absorbs a substantial portion of ultraviolet light radiation. Typical materials having this property include the following, either alone or in combination: glass, lithium fluoride, crystalline, "pyrex" numbers 9700 and 9741, para-aminobenzoic (5 percent alcohol) solution, ortho-aminobenzoates, anthranates, orthohydroxy benzoates, salicylates, 2-hydroxy-4 methoxybenzophenome (1 to 5 percent aqueous) solution, and 2-prime hydroxy-5 prime methyl phenyl benzotriazole (1 to 5 percent aqueous) solution.

Since substantially all harmful erythemal radiation occurs at wavelengths less than 320 nanometers, in the preferred embodiment filtering layer 12 is configured to substantially attenuate all wavelengths shorter than 320 nanometers and transmit the remaining wavelengths of the solar radiation spectrum. Filtering layer 12 is therefore configured as a low pass filter having a cutoff frequency corresponding to a wavelenth of 320 nanometers. If filtering layer 12 comprises glass, a one-inch-thick layer of glass provides the desired attenuation of ultraviolet light. In particular, a layer of such thickness has an absorptivity of 0.99 for radiation having wavelengths less than 320 nanometers. As a result, glass layer 12 advantageously filters off 99 percent of the harmful erythemal radiation in sunlight while transmitting all tanning radiation having wavelengths above 320 nanometers.

It will be appreciated by those skilled in the art that the thickness of filtering layer 12 determines its absorptivity. For example, in the preferred embodiment glass filtering layer 12 has a one-inch thickness, which provides an absorptivity of 0.99. In comparison, a one-eighth-inch thick layer of glass provides an absorptivity of 0.95. As a result, filtering layer 12 can be advantageously "tuned" to provide the desired absorptivity by the selection of an appropriate thickness for filtering layer 12.

As shown in FIG. 1, filtering layer 12 lies contiguous to reflecting layer 14 comprising base layer 17 and reflective surface layer 16. Base layer 17 comprises any rigid material and provides support for reflective surface layer 16. Reflective surface layer 16 comprises a highly reflective material such as silver or aluminum, which is either evaporation deposited onto base layer 17 or, if independently rigid such as a sheet of aluminum, bonded to base layer 17 with a bonding agent. The reflecting layer 14 is then bonded to filtering layer 12 with a transparent bonding agent.

To use the device, the user 30 orients the surface of filtering layer 12 and hence the surface of reflective surface layer 16 at such an angle to the solar radiation that the radiation reflected by the device strikes the person 30 as shown in FIG. 1. As previously discussed, the incident beam of solar radiation falls on filtering layer 12 at point 23 of the device. Band 21, which contains harmful erythemal radiation (i.e., wavelengths below 320 nanometers), is absorbed by the filtering layer 12 while band 22, which contains the tanning radiation and other remaining radiation in the solar radiation spectra, is transmitted through the layer as beam 24.

As will be appreciated by those skilled in the art, transmitted beam 24 is refracted by filtering layer 12 according to the index of refraction of the filter material so that transmitted beam 24 strikes reflecting layer 14 at point 25. Reflecting layer 14 reflects the beam so that reflected beam 26 strikes the end of filtering layer 12 opposite reflecting layer 14 at point 27. This beam then leaves the device at point 27, is refracted according to the index of refraction of air, and shines on the face of the user 30. Because beam 28 contains tanning radiation with little erythemal radiation, the device advantageously provides the user with a tan while shielding him from harmful erythemal radiation.

Because the device is not a lotion or cream, it eliminates many of the drawbacks of conventional ultraviolet screening agents which derive from their being in the form of lotions or creams which are applied directly to the skin. Although primarily oily, these agents are still soluble in water. Thus, perspiration of the user can dilute the agents or even completely wash them off, greatly reducing their effectiveness. In addition, the susceptibility of the chemicals in the lotion or cream to chemical and photochemical changes further decreases their ultraviolet absorbent effectiveness. Because it is difficult for the user to apply these agents to the body so that they form a continuous film of even thickness on the skin, they fail to promote uniform tanning Moreover, the chemicals in these agents frequently exhibit unpleasant odors.

As lotions or creams, these agents are easily absorbed through the skin. As a result, they can cause pathological side effects such as irritation, allergic responses, melanosis, and trophic changes in the skin, in addition to interfering with normal growth and metabolic processes of the skin and mucous membranes and associated organs. In addition, these agents may stain or cause residual staining to skin and clothing, especially in the presence of sunlight, heat, laundry detergents, perspiration, etc.

Figure 2:
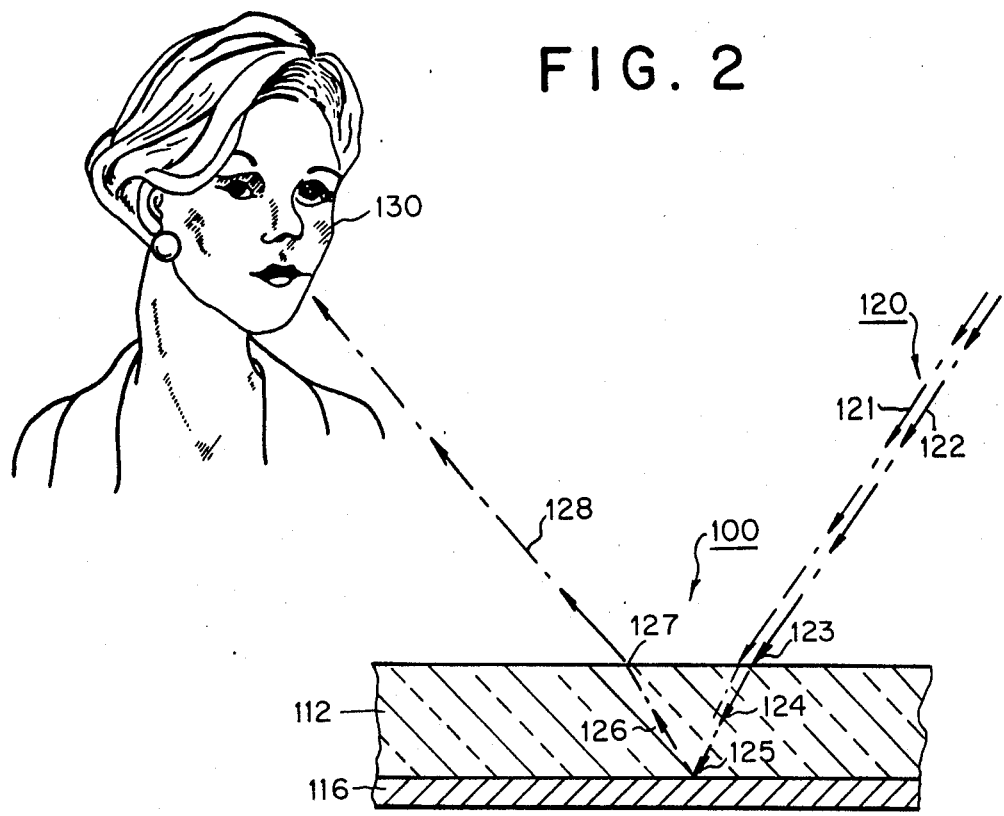
FIG. 2 is a cross-sectional view of another embodiment of the present invention.

FIG. 2 shows a cross-sectional view of a second preferred embodiment of the device and method of this invention. This device comprises many of the same elements as that of FIG. 1 and such elements bear the same numbers increased by 100. Unlike FIG. 1, however, this device does not have base layer 17. Instead, the reflective surface layer 116 is either evaporation deposited onto filtering layer 112 or, if independently rigid (i.e., self-supporting), bonded directly to filtering layer 112 with a bonding agent. Because this device operates in an identical manner to that of FIG. 1, the use of the device is similarly identical to FIG. 1.

Figure 3:
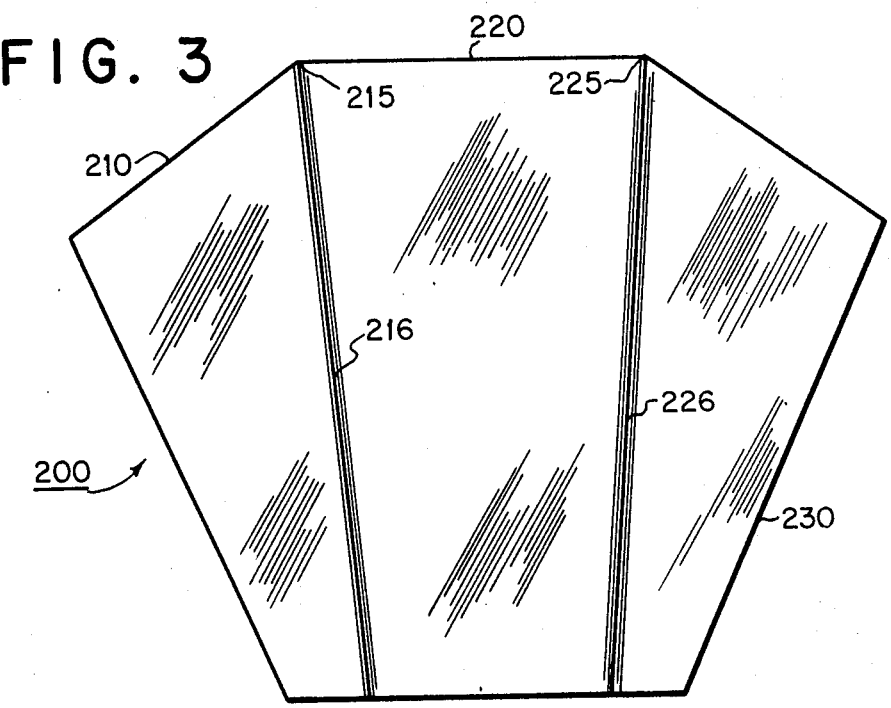
FIG. 3 is a plan view of an outer surface of the preferred embodiments shown in FIGS. 1 and 2.

FIG. 3 shows a plan view of an outer surface 200 of the preferred embodiments of the device shown in FIGS. 1 and 2 and, in particular, shows an outer surface of a filtering layer of the embodiments. Although surface 200 can be fabricated to form any number of panels, FIG. 3 shows the surface fabricated to form outer panels 210 and 230 and central panel 220. Moreover, although in FIG. 3 outer panels 210 and 230 are each shaped in the form of a quadrilateral and central panel 220 is shaped in the form of a trapezoid having parallel top and bottom edges, these panels can be fabricated to have any shape.

As shown in FIG. 3, the panels are fabricated from the initially surface device 200 by creasing it at two points, 215 and 225, along its width such that two creases, 216 and 226, extend the length of the device. In the alternative, creases 216 and 226 represent edges of the panels which are hinged together by any conventional hinging device. If panels 210, 220, and 230 are separate panels, they can be hinged along edges 216 and 226 of the device. Although as shown in FIG. 3, creases or hinges 216 and 226 are not perpendicular to the top and bottom edges of panel 220, they can be perpendicular to these edges. In addition, they can intersect the top and bottom edges of panel 220 at angles other than shown. By moving outer panels 210 and 230 about their respective creases or hinges 216 and 226, these outer panels can be angulated with respect to central panel 220. As a result, the surface 200 of the device can be advantageously conformed to the shape of any body segment that a user of the device desires to tan.

The present invention also advantageously provides a method of filtering radiation comprising the step of filtering from an incident radiation spectrum emitting from a source an absorption spectrum having a bandwidth of wavelengths corresponding to the bandwidth of wavelengths desired to be filtered and the step of reflecting all other bandwidths of wavelengths. In a preferred method for preventing sunburn, the method comprises the additional step of filtering all wavelengths having a bandwidth of less than 320 nanometers.

While the invention has been described in conjunction with specific embodiments, it is evident that numerous alternatives, modifications, and variations will be apparent to those skilled in the art in light of the foregoing description.

I claim:

1. A device for use in sun-tanning comprising:
    a first layer of filtering material having an absorption spectrum wherein substantially no less than one or more predetermined bandwidths of wavelengths unsuitable for use in sun-tanning are absorbed by said filtering material throughout a path taken by light through said layer, and
    a second layer of reflecting material contiguous to said layer of filtering material for reflecting substantially all wavelengths suitable for use in sun-tanning and substantially all of the wavelengths unsuitable for use in sun-tanning that remain to be absorbed by said filter layer.

2. The device of claim 1 wherein said layer of reflecting material comprises a sheet of aluminum.

3. The device of claim 1 wherein said layer of reflecting material is bonded to said layer of filtering material.

4. The device of claim 1 wherein said layer of reflecting material is evaporation deposited onto said layer of filtering material.

5. The device of claim 1 wherein a surface of said layer of reflecting material opposite said surface contiguous to said layer of filtering material is bonded to a layer of rigid material.

6. The device of claim 1 wherein a surface of said layer of reflecting material opposite said surface contiguous to said layer of filtering material is evaporation deposited onto a layer of rigid material.

7. A device for use in sun-taning comprising:
    a first layer of filtering material having an absorption spectrum wherein substantially no less than a bandwidth of wavelengths below 320 nanometers are absorbed by said filtering material throughout a path taken by light through said layer, and
    a second layer of reflecting material contiguous to said layer of filtering material for reflecting substantially all of the wavelengths suitable for use in sun-tanning and substantially all of the wavelengths unsuitable for use in sun-tanning that remain to be absorbed by said filter layer.

8. The device of claim 7 wherein said layer of reflecting material comprises a sheet of aluminum.

9. The device of claim 7 wherein said layer of reflecting material is bonded to said layer of filtering material.

10. The device of claim 7 wherein said layer of reflecting material is evaporation deposited onto said layer of filtering material.

11. The device of claim 7 wherein a surface of said layer of reflecting material opposite said surface contiguous to said layer of filtering material is bonded to a layer of rigid material.

12. The device of claim 7 wherein a surface of said layer of reflecting material opposite said surface contiguous to said layer of filtering material is evaporation deposited onto a layer of rigid material.

13. The device of claim 12 wherein said layer of reflecting material comprises aluminum.

14. The device of claim 12 wherein said layer of reflecting material comprises silver.

15. The device of claim 7 wherein said layer of filtering material comprises glass.

16. The device of claim 7 wherein said layer of filtering material comprises lithium fluouride crystalline.

17. The device of claim 7 wherein said layer of filtering material comprises para-aminobenzoic (5 percent alcohol) solution.

18. The device of claim 7 wherein said layer of filtering material comprises ortho-aminobenzoates.

19. The device of claim 7 wherein said layer of filtering material comprises anthranates.

20. The device of claim 7 wherein said layer of filtering material comprises orthohydroxy benzoates.

21. The device of claim 7 wherein said layer of filtering material comprises salicylates.

22. The device of claim 7 wherein said layer of filtering material comprises 2-hydroxy-4 methoxybenzophenome (1 to 5 percent aqueous) solution.

23. The device of claim 7 wherein said layer of filtering material comprises 2-prime hydroxy-5 prime methyl phenyl benzotriazole (1 to 5 percent aqueous) solution.

24. The device of claim 7 wherein said layer of filtering material comprises one or more layers comprising one or more materials which absorb a substantial portion of ultraviolet light radiation.

25. The device of claim 24 wherein said materials comprise: glass, lithium fluoride, crystalline, "pyrex" numbers 9700 and 9741, para-aminobenzoic (5 percent alcohol) solution, orthoaminobenzoates, anthranates, orthohydroxy benzoates, salicylates, 2-hydroxy-4 methoxybenzophenome (1 to 5 percent aqueous) solution, and 2-prime hydroxy-5 prime methyl phenyl benzotriazole (1 to 5 percent aqueous) solution.

26. The device of claim 7 wherein an outer surface of said device is fabricated to comprise one or more panels.

27. The device of claim 26 wherein crease means are provided between said panel or panels.

28. The device of claim 26 wherein hinge means are provided between said panel or panels.

29. The device of claim 26 wherein said outer surface of said device is fabricated to comprise two outer panels and a central panel.

30. The device of claim 29 wherein said outer panels are shaped in the form of a quadrilateral and said central panel is shaped in the form of a trapezoid having parallel top and bottom edges.

31. A method of filtering predetermined bandwidths of wavelengths unsuitable for use in sun-tanning comprising:

the step of filtering from an incident radiation spectrum emitting from a source an absorption spectrum having bandwidths substantially unsuitable for use in sun-tanning, and the step of reflecting substantially all other bandwidths of wavelengths.

32. The method of claim 31 wherein the step of filtering includes filtering all wavelengths having a wavelength less than 320 nanometers.

33. A device for use in sun-tanning comprising:
a first layer of reflecting material;
a second layer of filtering material contiguous on a first side to said reflecting layer;
wherein said filtering layer absorbs one or more predetermined bandwidths of wavelengths substantially unsuitable for use in sun-tanning throughout a path taken by light through said layer and said reflecting layer reflects substantially all of the wavelengths suitable for use in sun-tanning and substantially all of the wavelengths unsuitable for use in sun-tanning that remain to be absorbed by said filtering layer.

34. The device of claim 33 wherein said layer of reflecting material is bonded to said layer of filtering material.

35. The device of claim 33 wherein said layer of reflecting material is evaporation deposited onto said layer of filtering material.

36. The device of claim 33 wherein a surface of said layer of reflecting material opposite said surface contiguous to said layer of filtering material is bonded to a layer of rigid material.

37. The device of claim 33 wherein a surface of said layer of reflecting material opposite said surface contiguous to said layer of filtering material is evaporation deposited onto a layer of rigid material.

* * * * *